United States Patent [19]
Zimmermann

[11] Patent Number: 5,705,502
[45] Date of Patent: Jan. 6, 1998

[54] PHARMACOLOGICALLY ACTIVE PYRIMIDINEAMINE DERIVATIVES AND PROCESSES FOR THE PREPARATION THEREOF

[75] Inventor: Jürg Zimmermann, Wallbach, Switzerland

[73] Assignee: Novartis Corporation, Summit, N.J.

[21] Appl. No.: 446,742

[22] PCT Filed: Sep. 21, 1994

[86] PCT No.: PCT/EP94/03148

§ 371 Date: May 31, 1995

§ 102(e) Date: May 31, 1995

[87] PCT Pub. No.: WO95/09851

PCT Pub. Date: Apr. 13, 1995

[30] Foreign Application Priority Data

Oct. 1, 1993 [CH] Switzerland ............... 2968/93
Jul. 18, 1994 [CH] Switzerland ............... 2280/94

[51] Int. Cl.$^6$ ............... C07D 239/42; A61K 31/505
[52] U.S. Cl. ............... 514/275; 514/252; 544/295; 544/296; 544/238; 544/331
[58] Field of Search ............... 514/252, 275; 544/295, 331

[56] References Cited

U.S. PATENT DOCUMENTS 5,612,340 3/1997 Zimmermann ............... 514/252

*Primary Examiner*—John M. Ford
*Attorney, Agent, or Firm*—Gregory D. Ferraro

[57] ABSTRACT

Described are N-phenyl-2-pyrimidineamine derivatives of formula I (I)

wherein $R_1$ is a substituted cyclic radical, the cyclic radical being bonded at a ring carbon atom in each case and being selected from phenyl, pyridyl, pyrazinyl, thiazolyl, pyrimidinyl, pyridazinyl and imidazolyl, and the substituents of the above-mentioned cyclic radical being selected from one or more of the groups halogen, cyano, carbamoyl, —C(=O)—OR$_3$, —C(=O)—R$_4$, —SO$_2$—N(R$_5$)—R$_6$, —N(R$_7$)—R$_8$, —OR$_9$ and fluorine-substituted lower alkyl, wherein $R_3$, $R_4$, $R_5$, $R_6$, $R_7$, $R_8$ and $R_9$ are each independently of the others hydrogen or lower alkyl that is unsubstituted or substituted by mono- or di-lower alkylamino; and $R_2$ is selected from halogen, cyano, carbamoyl, —C(=O)—OR$_{10}$, —C(=O)—R$_{11}$, —SO$_2$—N(R$_{12}$)—R$_{13}$, —N(R$_{14}$)—R$_{15}$, —OR$_{16}$ and fluorine-substituted lower alkyl, wherein $R_{10}$, $R_{11}$, $R_{12}$, $R_{13}$, $R_{14}$, $R_{15}$ and $R_{16}$ are each independently of the others hydrogen or lower alkyl that is unsubstituted or substituted by mono- or di-lower alkylamino. Those compounds can be used, for example, in the treatment of tumour diseases.

9 Claims, No Drawings

PHARMACOLOGICALLY ACTIVE PYRIMIDINEAMINE DERIVATIVES AND PROCESSES FOR THE PREPARATION THEREOF

This application is filed under 35 U.S.C. § 371 as a national phase application of PCT/EP94/03148, filed Sep. 21, 1994 published as WO95/09851, Apr. 13, 1995.

The invention relates to N-phenyl-2-pyrimidineamine derivatives, to processes for the preparation thereof, to medicaments comprising those compounds, and to the use thereof in the preparation of pharmaceutical compositions for the therapeutic treatment of warm-blooded animals.

The invention relates to N-phenyl-2-pyrimidineamine derivatives of formula I

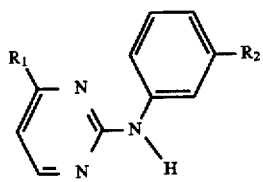

(I)

wherein $R_1$ is a substituted cyclic radical, the cyclic radical being bonded to a ring carbon atom in each case and being selected from phenyl, pyridyl, pyrazinyl, thiazolyl, pyrimidinyl, pyridazinyl and imidazolyl, and the substituents of the above-mentioned cyclic radical being selected from one or more of the groups halogen, cyano, carbamoyl, —C(=O)—OR$_3$, —C(=O)—R$_4$, —SO$_2$—N(R$_5$)—R$_6$, —N(R$_7$)—R$_8$, —OR$_9$ and fluorine-substituted lower alkyl, wherein $R_3$, $R_4$, $R_5$, $R_6$, $R_7$, $R_8$ and $R_9$ are each independently of the others hydrogen or lower alkyl that is unsubstituted or substituted by mono- or di-lower alkylamino; and $R_2$ is selected from halogen, cyano, carbamoyl, —C(=O)—OR$_{10}$, —C(=O)—R$_{11}$, —SO$_2$—N(R$_{12}$)—R$_{13}$, —N(R$_{14}$)—R$_{15}$, —OR$_{16}$ and fluorine-substituted lower alkyl, wherein $R_{10}$, $R_{11}$, $R_{12}$, $R_{13}$, $R_{14}$, $R_{15}$ and $R_{16}$ are each independently of the others hydrogen or lower alkyl that is unsubstituted or substituted by mono- or di-lower alkylamino, and to salts of such compounds having at least one salt-forming group.

A substituted cyclic radical $R_1$, such as, for example, a substituted phenyl radical $R_1$, can have several substituents, but especially not more than 3 and, especially in the case of relatively large substituents, preferably only one substituent, which substituents are principally in the para- (or 4-position) and/or preferably meta-position (or 3-position) with respect to the bonding site of the cyclic radical $R_1$. The above-mentioned substituted cyclic radicals $R_1$ other than phenyl generally have up to two and preferably only one substituent, which is/are especially in the para-position and/or preferably meta-position with respect to the bonding site of the cyclic radical $R_1$.

Pyridyl bonded to a ring carbon atom is 2- or preferably 4- or 3-pyridyl, especially 4-pyridyl. In a mono-substituted pyridyl radical $R_1$, the substituent is preferably in the ortho-position with respect to the pyridine nitrogen.

Halogen in a radical $R_1$ is preferably chlorine or fluorine.

Halogen-substituted phenyl $R_1$ is preferably 2-, 3- or 4-chloro-phenyl, 2,4-, 3,4- or 2,5-dichloro-phenyl or 2,3,4-trichloro-phenyl.

Fluorine-substituted lower alkyl $R_2$ is lower alkyl that carries at least one, but preferably several, fluorine substituents, especially 1,1,2,2-tetrafluoro-ethyl or more especially tri-fluoromethyl.

Mono- or di-lower alkylamino is, for example, methylamino or dimethylamino.

Within the scope of this text, the term "lower" denotes radicals having up to and including 7, preferably up to and including 4, carbon atoms.

Unless otherwise indicated in the context concerned, lower alkyl is preferably methyl or ethyl.

$R_3$ and $R_7$ are preferably hydrogen. $R_8$ is preferably lower alkyl, such as especially n-propyl. $R_9$ is preferably hydrogen or methyl.

Salt-forming groups in a compound of formula I are groups or radicals having basic or acidic properties. Compounds having at least one basic group or at least one basic radical, for example a mono-lower alkylamino group, a pyrazinyl radical or a pyridyl radical, can form acid addition salts, for example with inorganic acids, such as hydrochloric acid, sulfuric acid or a phosphoric acid, or with suitable organic carboxylic or sulfonic acids, for example aliphatic mono- or di-carboxylic acids, such as trifluoroacetic acid, acetic acid, propionic acid, glycolic acid, succinic acid, maleic acid, fumaric acid, hydroxymaleic acid, malic acid, tartaric acid, citric acid, oxalic acid or amino acids, such as arginine or lysine, aromatic carboxylic acids, such as benzoic acid, 2-phenoxy-benzoic acid, 2-acetoxy-benzoic acid, salicylic acid, 4-aminosalicylic acid, aromatic-aliphatic carboxylic acids, such as mandelic acid or cinnamic acid, heteroaromatic carboxylic acids, such as nicotinic acid or isonicotinic acid, aliphatic sulfonic acids, such as methane-, ethane- or 2-hydroxy-ethane-sulfonic acid, or aromatic sulfonic acids, for example benzene-, p-toluene- or naphthalene-2-sulfonic acid. If several basic groups are present, mono- or poly-acid addition salts can be formed.

Compounds of formula I having acidic groups, for example a free carboxy group in the radical $R_1$, can form metal or ammonium salts, such as alkali metal or alkaline earth metal salts, for example sodium, potassium, magnesium or calcium salts, or ammonium salts with ammonia or suitable organic amines, such as tertiary monoamines, for example tri-ethylamine or tri(2-hydroxyethyl)amine, or heterocyclic bases, for example N-ethyl-piperidine or N,N'-dimethyl-piperazine.

Compounds of formula I that possess both acidic and basic groups can form internal salts.

For the purpose of isolation or purification and also in the case of the compounds used further as intermediates, it is also possible to use pharmaceutically unacceptable salts. Only the pharmaceutically acceptable non-toxic salts are used therapeutically, however, and those are therefore preferred.

In view of the close relationship between the novel compounds in free form and in the form of their salts, including also salts that can be used as intermediates, for example in the purification of the novel compounds or in order to identify those compounds, hereinbefore and hereinafter any reference to the free compounds is to be understood as including also the corresponding salts, where appropriate and expedient.

The compounds of formula I exhibit valuable pharmacological properties: for example, they inhibit the enzyme protein kinase C with a high degree of selectivity. Phospholipid- and calcium-dependent protein kinase C occurs in cells in a number of forms and participates in various fundamental processes, such as signal transmission, proliferation and differentiation, and also the release of hormones and neurotransmitters. The activation of that enzyme is effected either by receptor-mediated hydrolysis of phospholipids of the cell membrane or by direct interaction with certain tumout-promoting active substances. The sensitivity of the cell to receptor-mediated signal transmission can be substantially influenced by modifying the activity of protein kinase C (as a signal transmitter). Compounds that are capable of influencing the activity of protein kinase C can be used as tumour-inhibiting, an antiinflammatory, immunomodulating and antibacterial active ingredients and may even be of value as agents against atherosclerosis and disorders of the cardiovascular system and central nervous system.

Formerly, porcine brain protein kinase C purified in accordance with the procedure described by T. Uchida and C. R. Filburn in J. Biol. Chem. 259, 12311–4 (1984) was used to determine the inhibitory action on protein kinase C, and the inhibitory action on protein kinase C was determined in accordance with the procedure of D. Fabbro et al., Arch. Biochem. Biophys. 239, 102–111 (1985).

The porcine brain protein kinase C formerly used is a mixture of various sub-types (isotypes) of protein kinase C. If pure recombinant isotypes are used instead of porcine brain protein kinase C in the above test it is found that the compounds of formula I inhibit the "conventional" isotype $\alpha$ preferentially whereas the other "conventional" isotypes $\beta$-1, $\beta$-2 and $\gamma$ and especially the "non-conventional" isotypes $\delta$, $\epsilon$ and $\eta$ and the "atypical" isoform $\zeta$ are generally inhibited to a distinctly lesser extent and in some cases hardly at all.

Recombinant PKC isotypes are cloned, expressed and purified in the following manner:

The production of various proteins with the aid of baculoviruses, and their cloning and isolation from Sf9 insect cells are carried out as described by M. D. Summers and G. E. Smith, "A manual method for baculovirus vectors and insect cell culture procedure", Texas Agricul. Exptl. Station Bull (1987), 1555. The construction and isolation of recombinant viruses for the expression of PKC-$\alpha$(bovine), PKC-$\beta$1(human), PKC-$\beta$2(human) and PKC-$\gamma$(human/bovine hybrid) in Sf9 cells are effected in the manner described by Stabel et al [S. Stabel, M. Liyanage and D. Frith, "Expression of protein kinase C isozymes in insect cells and isolation of recombinant proteins", Meth. Neurosc. (1993)]. The production of the PKC isotypes in Sf9 cells is carried out in the manner indicated by Stabel et al. (see above), and the purification of the enzymes is effected in accordance with the method described in the publication by McGlynn et al. [E. McGlynn, J. Liebetanz, S. Reutener, J. Wood, N. B. Lydon, H. Hofstetter, M. Vanek, T. Meyer and D. Fabbro, "Expression and partial characterization of rat protein kinase C-$\delta$ and protein kinase C-$\zeta$ in insect cells using recombinant baculovirus", J. Cell Biochem. 49, 239–250 (1992)]. For the generation of recombinant PKC-$\delta$(rat), PKC-$\epsilon$(rat), PKC-$\zeta$(rat) and PKC-$\eta$(mouse), and their expression and purification, the procedure described by Liyanage et al ["Protein kinase C group B members PKC-$\delta$, -$\epsilon$, -$\zeta$ and PKC-$\lambda$: Comparison of properties of recombinant proteins in vitro and in vivo", Biochem. J. 283, 781–787 (1992)] and McGlynn et al, respectively, (see above) is followed, with the additional feature that the transfer vector pAc360 is used for the expression of PKC-$\eta$ [V. Luckow and M. D. Summers, "Trends in the development of baculovirus expression", Biotechnology 6, 47–55 (1988)].

The measurement of the activity of the recombinant PKC isotypes obtained by the above method is carried out in the absence of lipid and calcium (co-factors). Protamine sulfate phosphorylated in the absence of co-factors is used as the substrate. The activity of the enzymes reflects the transfer of $^{32}$P from $\gamma$[$^{32}$P]-ATP to protamine sulfate. Protamine sulfate is a mixture of polypeptides each comprising four C-terminal arginine residues. Phosphate incorporation is measured under the following conditions: 100 $\mu$l of the reaction mixture comprise in final concentrations 20 mM TRIS-HCl pH 7.4, 10 mM Mg[NO$_3$]$_2$, 0.5 mg/ml of protamine sulfate, 10 $\mu$M ATP (0.1 $\mu$Ci $\gamma$-[$^{32}$P]-ATP; 10 Ci/mol; Amersham, Little Chalfont, United Kingdom), various concentrations of the inhibitory compounds and 0.5–2.5 U (units: a unit is the mount of enzyme that, in one minute and per milligram of protein, transfers one nanomole of $^{32}$P from the above-mentioned $\gamma$-[$^{32}$P]-ATP to histone H1 [Sigma, type V-S]) of the enzymes. The reaction is started by the addition of the enzymes and transfer at 32° C. The reaction time is 20 minutes. The reaction is then stopped by dripping aliquots of 50 $\mu$l onto P81 chromatography paper (Whatman, Maidstone, United Kingdom). After removing unbound $\gamma$[$^{32}$P]-ATP and nucleotide fragments by washing operations as described by J. J. Witt and R. Roskoski, "Rapid protein kinase assay using phospho-cellulose-paper absorption", Anal. Biochem. 66, 253–258 (1975), the substrate phosphorylation is determined by scintillation measurement. In that test, the compounds of formula I inhibit the $\alpha$-isotype of protein kinase C (PKC) at an IC$_{50}$ of as low as approximately from 1 to 75 $\mu$mol/liter, generally approximately from 1 to 10 $\mu$mol/liter. In contrast, the other isotypes of PKC are generally inhibited only at distinctly higher concentrations (i.e. at concentrations up to more than 300 times higher).

As may be expected purely on the basis of the above-described inhibitory action on protein kinase C, the compounds of formula I exhibit antiproliferative properties which can be demonstrated directly in another test described in the following in which the inhibitory action of the compounds of formula I on the growth of human T24 bladder carcinoma cells is determined. Those cells are incubated in Eagle's minimal essential medium, to which 5% (v/v) foetal calf serum has been added, in a humidified incubator at 37° C. and with 5% by volume of CO$_2$ in the air. The carcinoma cells (1000–1500) are sown in 96-well microtitre plates and incubated overnight under the above-mentioned conditions. The test compound is added in serial dilutions on day 1. The plates are incubated for 5 days under the above-mentioned conditions. During that period the control cultures undergo at least four cell divisions. After incubation, the cells are fixed with 3.3% (w/v) aqueous glutaraldehyde solution, washed with water and stained with 0.05% (weight/volume) aqueous methylene blue solution. After washing, the dye is eluted with 3% (w/v) aqueous hydrochloric acid. The optical density (OD) per well, which is directly proportional to the number of cells, is then measured at 665 nm using a photometer (Titertek multiskan). The IC$_{50}$ values are calculated with a computer system using the formula $$\frac{OD_{665} \text{ (test) minus } OD_{665} \text{ (start)}}{OD_{665} \text{ (control) minus } OD_{665} \text{ (start)}} \times 100$$

The IC$_{50}$ values are defined as being the concentration of active ingredient at which the number of cells per well at the end of the incubation period is only 50% of the number of cells in the control cultures. In the case of the compounds of formula I, the IC$_{50}$ values so ascertained are generally approximately from 1 to 20 $\mu$mol/liter.

The anti-tumour activity of the compounds of formula I can also be demonstrated in vivo:

Female Balb/c hairless mice with s.c. transplanted human bladder tumours T24 are used to determine the anti-tumour activity. On day 0, with the animals under peroral forene narcosis, approximately 25 mg of a solid tumour are placed under the skin on the animals' left flank and the small incised wound is closed by means of suture clips. On day 6 after the transplantation, the mice are divided at random into groups of 6 animals and treatment commences. The treatment is carried out for 15 days with peroral or intraperitoneal administration once daily of a compound of formula I in dimethyl sulfoxide/Tween 80/-sodium chloride solution in the various doses. The tumours are measured twice a week with a slide gauge and the volume of the tumours is calculated. In that test, the peroral or intraperitoneal administration of a compound of formula I brings about a marked reduction in the avenge tumour volume in comparison with the untreated control animals.

On the basis of the properties described, the compounds of formula I can be used especially as tumour-inhibiting active ingredients, for example in the treatment of tumours of the bladder and the skin. When the compounds of formula I are used in the treatment of cancer in combination with other chemotherapeutic drugs, they prevent the development of resistance (multidrug resistance) or eliminate an already existing resistance to the other chemotherapeutic drugs. They are also suitable for the other uses mentioned above for protein kinase C modulators and can be used especially in the treatment of disorders responsive to inhibition of protein kinase C.

Some of the compounds of formula I also inhibit the tyrosine kinase activity of the receptor for the epidermal growth factor (EGF). That receptor-specific enzyme activity plays a key role in signal transmission in a large number of mammalian cells, including human cells, especially epithelial cells, cells of the immune system and cells of the central and peripheral nervous system. In the case of various types of cell, the EGF-induced activation of the receptor-associated tyrosine protein kinase (EGF-R-TPK) is a prerequisite for cell division and accordingly for the proliferation of a cell population. The addition of EGF-receptor-specific tyrosine kinase inhibitors thus inhibits the replication of those cells.

Inhibition of EGF-receptor-specific tyrosine protein kinase (EGF-R-TPK) can be demonstrated, for example, using the method of E. McGlynn et al, Europ. J. Biochem. 207, 265–275 (1992). The compounds according to the invention inhibit the enzyme activity by 50% (IC50) for example at a concentration of from 0.1 to 10 μM.

The compounds of formula I that inhibit the tyrosine kinase activity of the receptor for the epidermal growth factor (EGF) can accordingly be used, for example, in the treatment of benign or malignant tumours. They are able to bring about tumour regression and to prevent metastatic spread and the growth of micrometastases. They can be used especially in the case of epidermal hyperproliferation (psoriasis), in the treatment of neoplasia of epithelial character, for example mastocarcinoma, and in the case of leukaemia. The compounds can also be used in the treatment of disorders of the immune system and inflammation if protein kinases are involved. Furthermore, those compounds of formula I can be used in the treatment of disorders of the central or peripheral nervous system if signal transmission by protein kinases is involved.

The compounds of formula I and salts of such compounds having at least one salt-forming group also inhibit the enzyme $p34^{cdc2}$/cycline $B^{cdc13}$ kinase. That kinase controls, in addition to other cdc2-related kinases, specific phases of cell division, especially the transition from the $G_1$-phase to the S-phase and more especially the transition from the $G_2$-phase to the M-phase.

In chronological order, the cycle of a eukaryotic cell consists of the interphase and the M-phase. The interphase is accompanied by an increase in the size of the cell. In chronological order, the interphase consists for its part of the $G_1$-phase, the S-phase and the $G_2$-phase. In the $G_1$-phase (G=gap) biosynthetic processes take place in the cell. In the S-phase (synthesis phase) the DNA doubles. The cell then enters the $G_2$-phase which ends with the commencement of mitosis.

In chronological order, the M-phase for its part consists of the division of the cell nucleus (mitosis) and the division of the cytoplasm (cytokinesis).

The above-mentioned inhibition of the enzyme $p34^{cdc2}$/cycline $B^{cdc13}$ kinase can be demonstrated by the following test;

10 μM 1-methyl-adenine are used to induce starfish oocytes to enter the M-phase. The oocytes are then frozen in liquid nitrogen and stored at −80° C. If necessary, the oocytes are homogenised and centrifuged, as described in D. Arion et al, Cell 55, 371–378 (1988) and V. Rialet and L. Meijer, Anticancer Res. 11, 1581–1590 (1991). In order to purify the $p34^{cdc2}$/cycline $B^{cdc13}$ kinase, the supernatant of the oocytes is added to $p9^{CKShs}$-Sepharose grains prepared from recombinant human protein $p9^{CKShs}$, as described in L. Azzi et al., Eur. J. Biochem. 203, 353–360 (1992). After 30 minutes at 4° C. while being turned constantly, the grains are washed thoroughly and the active $p34^{cdc2}$/cycline $B^{cdc13}$ kinase is eluted with free protein $p9^{CKShs}$ (3 mg/ml). The eluted kinase is tested using historic H1 as substrate, as described in L. Meijer et al., EMBO J. 8, 2275–2282 (1989) and EMBO J. 10, 1545–1554 (1991). In that test, the compounds of formula I and salts of such compounds having at least one salt-forming group exhibit an inhibiting concentration IC50[μmol/liter] of approximately from 0.01 to 2.

That finding would also lead to the expectation that the compounds of formula I and salts of such compounds having at least one salt-forming group can be used in the treatment of hyperproliferative disorders, such as tumours and psoriasis.

The compounds of formula I also inhibit the production of HIV viruses, as shown by the test below, and can accordingly be used as agents against the immune deficiency disease AIDS. The initial symptoms observed after HIV infection in humans is followed by a clinical latency period which can last several years. After that period, the stage known as AIDS occurs and usually progresses to death. The latency period is attributed to several factors: immune response, occlusion of the viruses in lymph nodes or other tissue and entry into a stage of molecular and viral latency in which the infected cells do not complete the viral cell cycle, which is why infectious viruses cannot be produced and the infection cannot spread. That stage of molecular latency has been investigated using cell models, such as the ACH-2 cell line [K. Clouse et al., J. Immunol. 142, 431 (1989)] and the U1 cell line [T. Folks et al., J. Immunol. 140, 117 (1988)]. Those cells are infected with HIV-1 viruses, but have only a low content of infectious viruses. If, however, those cells are stimulated with physiologically relevant factors that are known to be increased in AIDS patients, such as tumour necrosis factor, interleukin-6 etc., or with chemical inductors, such as phorbol diesters for example 13-O-acetyl-12-O-n-tetradecanoyl-phorbol, a massive production of virus follows. The ACH-2 and U1 cells are representatives of two different cell families that are targets for HIV infection, namely lymphocytes and macrophages.

Hitherto, effective prevention of the progression of HIV infection to the outbreak of AIDS has not been possible.

Many attempts have been made to prevent virus replication after the outbreak of AIDS, that is to say, in a stage in which viruses are produced on a massive scale. In contrast, the compounds of formula I interfere with cell processes that lead to the activation of latently infected HIV cells without impairing normal cell processes, such as cell division.

If the above-mentioned U 1 or ACH-2 cells are used as a model for viral latency, it can be demonstrated that HIV virus production induced by 13-O-acetyl-12-O-n-tetradecanoyl-phorbol or tumour necrosis factor-alpha are effectively inhibited by the compounds of formula I at a concentration of approximately from 0.001 to 1 µmol/liter, for example at 0.03 µmol/liter.

Preferred are compounds of formula I wherein $R_1$ is substituted pyridyl bonded to a ring carbon atom, the substituents of the above-mentioned pyridyl radical being selected from halogen, cyano, carbamoyl, —C(=O)—OR$_3$, —N(R$_7$)—R$_8$ and —OR$_9$, wherein $R_3$, $R_7$, $R_8$ and $R_9$ are each independently of the others hydrogen or lower alkyl; and $R_2$ is selected from halogen, —C(=O)—OR$_{10}$, wherein
   $R_{10}$ is hydrogen or lower alkyl,
   and from fluorine-substituted lower alkyl,
   and salts of such compounds having at least one salt-forming group.

Preferred are especially compounds of formula I wherein $R_1$ is a pyridyl radical substituted by halogen, cyano, carboxy, carbamoyl, hydroxy or by N-lower alkyl-amino, and $R_2$ is halogen or fluorine-substituted lower alkyl, and the salts thereof.

Especially preferred are compounds of formula I wherein $R_1$ is a 4-pyridyl radical substituted in the 2-position by chlorine, cyano, carboxy, carbamoyl, hydroxy or by N-propyl-amino and R2 is chlorine or trifluoromethyl, and the salts thereof.

Very preferred are also compounds of formula I wherein $R_1$ is a 4-pyridyl radical substituted in the 2-position with respect to the pyridine nitrogen by chlorine, cyano, carboxy, carbamoyl, hydroxy, amino, N-propyl-amino, N,N-dimethylamino or by N-butyl-amino, and $R_2$ is chlorine, trifluoromethyl, carboxy or lower alkoxycarbonyl, and the salts thereof.

More especially preferred are the compounds of formula I described in the Examples.

The compounds of formula I and the salts of such compounds having at least one salt-forming group are prepared in accordance with processes known per se. The process according to the invention is effected as follows:

a) a compound of formula II

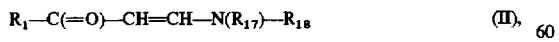

wherein $R_{17}$ and $R_{18}$ are each independently of the other lower alkyl and $R_1$ is as defined above, functional groups present in a compound of formula II, with the exception of the groups participating in the reaction, being, if necessary, in protected form, or a salt of such a compound is reacted with a compound of formula III

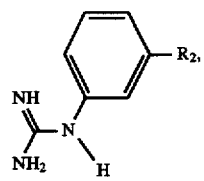

wherein $R_2$ is as defined above, functional groups present in a compound of formula III, with the exception of the guanidino group participating in the reaction, being, if necessary, in protected form, or with a salt of such a compound, and any protecting groups present are removed, or b) for the preparation of a compound of formula I wherein $R_1$ is pyridyl, pyrazinyl thiazolyl, pyrimidinyl, pyridazinyl or imidazolyl, each of which is substituted by a radical of the formula —N(R$_7$)—R$_8$, and $R_2$ has any one of the above-mentioned meanings, a compound of formula I wherein $R_1$ is pyridyl, pyrazinyl, thiazolyl, pyrimidinyl, pyridazinyl or imidazolyl, each of which is substituted by a leaving group, is reacted with an amine of formula HN(R$_7$)  (IV), wherein the substituents are as defined above, functional groups present in a compound of formula IV, with the exception of the amino group participating in the reaction, being, if necessary, in protected form, and any protecting groups present are removed, or c) for the preparation of a compound of formula I wherein $R_1$ is any one of the above-mentioned cyclic radicals substituted by carbamoyl or by a radical of the formula —C(=O)—OR$_3$, wherein $R_3$ is hydrogen, and $R_2$ has any one of the above-mentioned meanings, a compound of formula I wherein $R_1$ is any one of the above-mentioned cyclic radicals substituted by cyano is hydrolysed, or d) for the preparation of a compound of fomula I nwherein $R_1$ is a pyridyl radical substituted by cyano or by —OR$_9$, wherein $R_9$ is hydrogen or lower alkyl, and $R_2$ has any one of the above-mentioned meanings, in an N-oxido-pyridyl compound of formula VIII

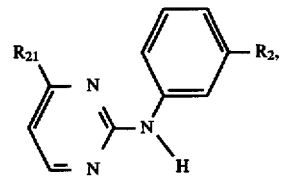

wherein $R_{21}$ is N-oxido-pyridyl bonded to a ring carbon atom and $R_2$ has any one of the above-mentioned meanings, the N-oxido group is converted into a leaving group and the resulting leaving group is removed from the molecule by nucleophilic substitution in the ortho-position with respect to the pyridyl nitrogen using a nucleophile that introduces hydroxy, cyano or unsubstituted or halogen-substituted lower alkoxy, or e) for the preparation of a compound of formula I wherein $R_1$ is a pyridyl radical substituted by chlorine and $R_2$ has any one of the above-mentioned meanings, an N-oxido-pyridyl compound of formula VIII

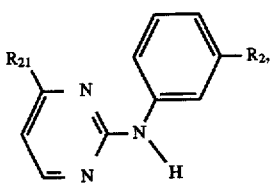

(VIII)

wherein $R_{21}$ is N-oxido-pyridyl bonded to a ring carbon atom and $R_2$ has any one of the above-mentioned meanings, is reacted with a reagent that introduces chlorine in the ortho-position with respect to the N-oxido group, and, if desired, a compound of formula I obtainable in accordance with any one of Process a–e is converted into its salt, or an obtainable salt of a compound of formula I is converted into the free compound.

The manner in which the above-mentioned process variants are carried out is explained in detail hereinafter.

General

The end products of formula I may comprise substituents that can also be used as protecting groups in starting materials for the preparation of other end products of formula I. Within the scope of this text, therefore, unless the context indicates otherwise, only a readily removable group that is not a constituent of the particular end product of formula I desired is referred to as a "protecting group".

Protecting groups and the manner in which they are introduced and removed are described, for example, in "Protective Groups in Organic Chemistry", Plenum Press, London, New York 1973, and in "Methoden der organischen Chemie", Houben-Weyl, 4th edition, Vol. 15/1, Georg-Thieme-Verlag, Stuttgart 1974 and in Theodora W. Greene, "Protective Groups in Organic Synthesis", John Wiley & Sons, New York 1981. A characteristic of protecting groups is that they can be readily removed, that is to say, without undesired secondary reactions taking place, for example by solvolysis, reduction, photolysis or also under physiological conditions.

Hydroxy-protecting groups are, for example, acyl radicals, such as unsubstituted or substituted, for example halogen-substituted, lower alkanoyl, such as 2,2-dichloroacetyl, or acyl radicals of carbonic acid semiesters, especially tert-butoxycarbonyl, unsubstituted or substituted benzyloxycarbonyl, for example 4-nitrobenzyloxycarbonyl, or diphenylmethoxycarbonyl, or 2-halo-lower alkoxycarbonyl, such as 2,2,2-trichloroethoxycarbonyl, and also trityl or formyl, or organic silyl or stannyl radicals, and also readily removable etherifying groups, such as left-lower alkyl, for example tert-butyl, 2-oxa- or 2-thia-aliphatic or -cycloaliphatic hydrocarbon radicals, especially 1-lower alkoxy-lower alkyl or 1-lower alkylthio-lower alkyl, for example methoxymethyl, 1-methoxy-ethyl, 1-ethoxyethyl, methylthiomethyl, 1-methylthioethyl or 1-ethylthioethyl, or 2-oxa- or 2-thia-cycloalkyl having 5 or 6 ring atoms, for example tetrahydrofuryl or 2-tetrahydropyranyl or corresponding this analogues, and also unsubstituted or substituted 1-phenyl-lower alkyl, such as unsubstituted or substituted benzyl or diphenylmethyl, suitable substituents of the phenyl radicals being, for example, halogen, such as chlorine, lower alkoxy, such as methoxy, and/or nitro.

A protected amino group may, for example, be in the form of a readily cleavable acylamino, arylmethylamino, etherified mercaptoamino, 2-acyl-lower alk-1-en-yl-amino, silylamino or stannylamino group or in the form of an azido group.

In a corresponding acylamino group, acyl is, for example, the acyl radical of an organic carboxylic acid having, for example, up to 18 carbon atoms, especially of an alkanecarboxylic acid that is unsubstituted or substituted, for example, by halogen or by aryl, or of a benzoic acid that is unsubstituted or substituted, for example, by halogen, lower alkoxy or by nitro, or of a carbonic acid semiester. Such acyl groups are, for example, lower alkanoyl, such as formyl, acetyl or propionyl, halo-lower alkanoyl, such as 2-haloacetyl, especially 2-chloro-, 2-bromo-, 2-iodo-, 2,2,2-trifluoro- or 2,2,2-trichloro-acetyl, benzoyl that is unsubstituted or substituted, for example, by halogen, lower alkoxy or by nitro, for example benzoyl, 4-chlorobenzoyl, 4-methoxybenzoyl or 4-nitrohenzoyl, or lower alkoxycarbonyl that is branched in the 1-position of the lower alkyl radical or suitably substituted in the 1- or 2-position, especially tert-lower alkoxycarbonyl, for example tert-butoxycaxbonyl, arylmethoxycarbonyl having one or two aryl radicals that are preferably phenyl that is unsubstituted or mono- or poly-substituted, for example, by lower alkyl, especially left-lower alkyl, such as tert-butyl, lower alkoxy, such as methoxy, hydroxy, halogen, for example chlorine, and/or by nitro, such as unsubstituted or substituted benzyloxycarbonyl, for example 4-nitrobenzyloxycarbonyl, or substituted diphenylmethoxycarbonyl, for example benzhydryloxycarbonyl or di(4-methoxyphenyl) methoxycarbonyl, aroylmethoxycarbonyl wherein the aroyl group is preferably benzoyl that is unsubstituted or substituted, for example, by halogen, such as bromine, for example phenacyloxycarbonyl, 2-halo-lower alkoxycarbonyl, for example 2,2,2-trichloroethoxycarbonyl, 2-bromoethoxycarbonyl or 2-iodoethoxycarbonyl, or 2-(trisubstituted silyl)ethoxycarbonyl wherein the substituents are each independently of the others an aliphatic, araliphatic, cycloaliphatic or aromatic hydrocarbon radical that is unsubstituted or substituted, for example, by lower alkyl, lower alkoxy, aryl, halogen or by nitro, and contains up to 15 carbon atoms, such as corresponding unsubstituted or substituted lower alkyl, phenyl-lower alkyl, cycloalkyl or phenyl, for example 2-tri-lower alkylsilylethoxycarbonyl, such as 2-trimethylsilylethoxycarbonyl or 2-(di-n-butyl-methyl-silyl)-ethoxycarbonyl, or 2-triarylsilylethoxycarbonyl, such as 2-triphenylsilylethoxycarbonyl.

Other acyl radicals suitable as amino-protecting groups are also corresponding radicals of organic phosphoric, phosphonic or phosphinic acids, such as di-lower alkylphosphoryl, for example dimethylphosphoryl, diethylphosphoryl, di-n-propylphosphoryl or diisopropylphosphoryl, dicycloalkylphosphoryl, for example dicyclohexylphosphoryl, unsubstituted or substituted diphenylphosphoryl, for example diphenylphosphoryl, unsubstituted or substituted, for example nitro-substituted, di(phenyl-lower alkyl)phosphoryl, for example dibenzylphosphoryl or di(4-nitrobenzyl)phosphoryl, unsubstituted or substituted phenyloxyphenylphosphonyl, for example phenyloxyphenylphosphonyl, di-lower alkylphosphinyl, for example diethylphosphinyl, or unsubstituted or substituted diphenylphosphinyl, for example diphenylphosphinyl.

In an arylmethylamino group that is a mono-, di- or, especially, tri-arylmethylamino group, the aryl radicals are especially unsubstituted or substituted phenyl radicals. Such groups are, for example, benzyl-, diphenylmethyl- and, especially, trityl-amino.

An etherified mercapto group in an amino group protected by such a radical is especially arylthio or aryl-lower alkylthio wherein aryl is especially phenyl that is unsubstituted or substituted, for example, by lower alkyl, such as methyl or tert-butyl, lower alkoxy, such as methoxy, halogen, such as chlorine, and/or by nitro. A corresponding amino-protecting group is, for example, 4-nitrophenylthio.

In a 2-acyl-lower alk-1-en-1-yl radical that can be used as an amino-protecting group, acyl is, for example, the corresponding radical of a lower alkanecarboxylic acid, of a benzoic acid that is unsubstituted or substituted, for example, by lower alkyl, such as methyl or tert-butyl, lower alkoxy, such as methoxy, halogen, such as chlorine, and/or by nitro, or especially of a carbonic acid semiester, such as a carbonic acid lower alkyl semiester. Corresponding protecting groups are especially 1-lower alkanoyl-prop-1-en-2-yl, for example 1-acetyl-prop-1-en-2-yl, or 1-lower alkoxycarbonyl-prop-1-en-2-yl, for example 1-ethoxycarbonyl-prop-1-en-2-yl.

Preferred amino-protecting groups are acyl radicals of carbonic acid semiesters, especially tert-butoxycarbonyl, benzyloxycarbonyl that is unsubstituted or substituted, for example, as indicated, for example 4-nitrobenzyloxycarbonyl, or diphenylmethoxycarbonyl, or 2-halo-lower alkoxycarbonyl, such as 2,2,2-trichloroethoxycarbonyl, and also trityl or formyl. The removal of the protecting groups that are not constituents of the desired end product of formula I is effected in a manner known per se, for example by solvolysis, especially hydrolysis, alcoholysis or acidolysis, or by means of reduction, especially hydrogenolysis or chemical reduction, as appropriate stepwise or simultaneously.

A protected amino group is freed in a manner known per se and, depending on the nature of the protecting groups, in various manners, preferably by solvolysis or reduction. 2-halo-lower alkoxycarbonylamino (where appropriate after conversion of a 2-bromo-lower alkoxycarbonylamino group into a 2-iodo-lower alkoxycarbonylamino group), aroylmethoxycarbonylamino or 4-nitrobenzyloxycarbonylamino can be cleaved, for example, by treatment with a suitable chemical reducing agent, such as zinc in the presence of a suitable carboxylic acid, such as aqueous acetic acid. Aroylmethoxycarbonylamino can also be cleaved by treatment with a nucleophilic, preferably salt-forming reagent, such as sodium thiophenolate, and 4-nitro-benzyloxycarbonylamino also by treatment with an alkali metal dithionite, for example sodium dithionite. Unsubstituted or substituted diphenylmethoxycarbonylamino, left-lower alkoxycarbonylamino or 2-tri-substituted silylethoxycarbonylamino can be cleaved by treatment with a suitable acid, for example formic acid or trifluoroacetic acid, unsubstituted or substituted benzyloxycarbonylamino, for example, by hydrogenolysis, that is to say by treatment with hydrogen in the presence of a suitable hydrogenation catalyst, such as a palladium catalyst, unsubstituted or substituted triarylmethylamino or formylamino, for example, by treatment with an acid, such as a mineral acid, for example hydrochloric acid, or an organic acid, for example formic, acetic or trifluoroacetic acid, where appropriate in the presence of water, and an amino group protected by an organic silyl group can be freed, for example, by hydrolysis or alcoholysis. An amino group protected by 2-haloacetyl, for example 2-chloroacetyl, can be freed by treatment with thiourea in the presence of a base, or with a thiolate salt, such as an alkali metal thiolate, of the thiourea, and subsequent solvolysis, such as alcoholysis or hydrolysis, of the resulting condensation product. An amino group protected by 2-substituted silylethoxycarbonyl can also be converted into the free amino group by treatment with a hydrofluoric acid salt yielding fluoride anions.

A hydroxy group protected by a suitable acyl group, an organic silyl group or by unsubstituted or substituted 1-phenyl-lower alkyl is freed analogously to a correspondingly protected amino group. Hydroxy protected by unsubstituted or substituted 1-phenyl-lower alkyl, for example benzyl, is freed preferably by catalytic hydrogenation, for example in the presence of a palladium-on-carbon catalyst. A hydroxy group protected by 2,2-dichloroacetyl is freed, for example, by basic hydrolysis, and a hydroxy group etherified by tert-lower alkyl or by a 2-oxa- or 2-thiaaliphatic or -cycloaliphatic hydrocarbon radical is freed by acidolysis, for example by treatment with a mineral acid or a strong carboxylic acid, for example trifluoroacetic acid. Hydroxy etherified by an organic silyl radical, for example trimethylsilyl, can also be freed by a hydrofluoric acid salt yielding fluoride anions, for example tetrabutylammonium fluoride.

Process a

Preferably, $R_{17}$ and $R_{18}$ are each methyl.

Free functional groups in a compound of formula II, which are advantageously protected by readily removable protecting groups, are especially amino groups in the radical $R_1$.

Free functional groups in a compound of formula III, which are advantageously protected by readily removable protecting groups, are especially amino groups, but also hydroxy and carboxy groups.

A salt of a compound of formula II or III is preferably an acid addition salt, for example a nitrate or one of the acid addition salts mentioned for the end products of formula I.

The reaction is carried out in a suitable solvent or dispersing agent, for example a suitable alcohol, such as 2-methoxy-ethanol or a suitable lower alkanol, for example isopropanol or isobutanol, at a temperature of from room temperature (approximately 20° C.) to 150° C., for example under reflux. Especially when the compound of formula II is used in the form of a salt, that salt is converted into the free compound, preferably in situ, by the addition of a suitable base, such as an alkali metal hydroxide, for example sodium hydroxide.

The starting material of formula II is obtained by reacting a compound of formula V

(V)

wherein $R_1$ is as defined above, with a compound of formula VI

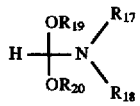

(VI)

wherein $R_{19}$ and $R_{20}$ are each lower alkyl and the other substituents are as defined above, analogously to the procedure described in the European Patent Application having the publication number 233 461. Typical representatives of a compound of formula VI are N,N-dimethylformamide dimethylacetal and N,N-dimethylformamide diethylacetal. The reaction is effected while heating the reactants of formulae V and VI, for example for 1–24 hours, in the absence or, if necessary, in the presence of a solvent, at a temperature of approximately from 50° C. to 150° C.

Alternatively, the starting material of formula II can also be obtained by reacting a compound of formula V with formic acid ethyl ester of the formula H—C(=O)—O—CH$_2$—CH$_3$ and reacting the resulting product with an amine of the formula H—N(R$_{17}$)—R$_{18}$ wherein the substituents are as defined above.

The starting material of formula III is obtained in the form of an acid addition salt by reacting an aniline derivative of formula VII

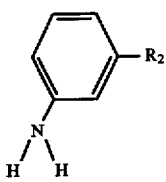
(VII)

wherein R₂ is as defined above, with cyanamide (NC—NH₂). The reaction is effected in a suitable solvent or dispersing agent, for example a suitable alcohol, for example a suitable lower alkanol, such as ethanol, for example α) in the presence of equimolar amounts of the salt-forming acid, for example nitric acid, or β) in the presence of a clear, for example 60%, excess of a mineral acid, such as hydrochloric acid, an ammonium salt of the desired salt-forming acid, for example ammonium nitrate, being added when the reaction is complete, at a temperature of from room temperature to 150° C., for example under reflux.

Process b

A leaving group is reactive esterified hydroxy, for example hydroxy esterified by a strong inorganic or organic acid, such as by a mineral acid, for example a hydrohalic acid, such as hydrochloric, hydrobromic or hydriodic acid, also sulfuric acid or a sulfuryl halide, for example sulfuryl fluoride, or by a strong organic sulfonic acid, such as a lower alkanesulfonic acid that is unsubstituted or substituted, for example, by halogen, such as fluorine, or an aromatic sulfonic acid, for example a benzenesulfonic acid that is unsubstituted or substituted by lower alkyl, such as methyl, halogen, such as bromine, and/or by nitro, for example a methanesulfonic, trifluoromethanesulfonic or p-toluenesulfonic acid. A preferred leaving group is halogen, such as, especially, chlorine.

The reaction is preferably carried out in the presence of an excess of the amine of formula IV, which can, where appropriate, also be used as solvent, and, if necessary, in the presence of an inert solvent, such as dimethyl sulfoxide, at a temperature of from room temperature to +150° C., for example at 100° C.

Process c

The hydrolysis of cyano to carbamoyl can be carried out in the presence of a suitable weak base, such as an alkali metal carbonate, for example sodium carbonate. In order to prevent the hydrolysis from continuing partially to carboxy, it is recommendable to carry out the hydrolysis with hydrogen peroxide in the presence of a suitable olefin, such as preferably a lower alkene, for example 1-hexene, in the presence of an alkali metal carbonate, for example sodium carbonate, in a suitable solvent, such as an alcohol, such as preferably ethanol, at more temperature.

The hydrolysis of cyano to carboxy is carried out in a suitable solvent, such as an alcohol, such as ethanol, for example in the presence of a suitable base, such as aqueous sodium hydroxide solution, at temperatures of from room temperature to +150° C., for example at 60° C.

Process d

The conversion of the N-oxide group into a leaving group is effected, for example, by reaction with a suitable reactive carboxylic or sulfonic acid derivative, for example with a suitable lower alkanoic acid chloride, lower alkanoic acid anhydride, such as acetic anhydride, N,N-dimethylcarbamoyl chloride, toluenesulfonyl chloride, methanesulfonyl chloride or trifluoromethanesulfonyl chloride. A nucleophile that introduces cyano is, for example, a suitable silyl cyanide, such as tri-lower alkyl-silyl cyanide, for example tri-methylsilyl cyanide. A nucleophile that introduces lower alkoxy or halogen-substituted lower alkoxy is, for example, a corresponding lower alkanol, or a suitable metal salt, such as, for example, an alkali metal salt, thereof, that is to say, a corresponding lower alkanolate. Hydroxy can be introduced, for example, by reacting a compound of formula VIII with a suitable acid anhydride and hydrolysing the resulting intermediate.

Process d is carried out in a suitable solvent, such as acetonitrile, at temperatures of approximately from 0° C. to 150° C., preferably approximately from room temperature to 100° C.

The starting material of formula VIII is obtained, for example, by oxidising a corresponding pyridyl compound analogous to formula VIII, wherein $R_{21}$ is pyridyl bonded to a ring carbon atom, with a suitable oxidising agent, such as hydrogen peroxide or a suitable peracid, for example a suitable perbenzoic acid, such as especially m-chloroperbenzoic acid, in an inert solvent, such as methylene chloride, at room temperature.

Alternatively, the starting material of formula VIII can be obtained, for example, by first oxidising acetyl-pyridine, such as 4-acetyl-pyridine, with m-chloro-perbenzoic acid in a suitable solvent, such as methylene chloride, for example under reflux, to acetyl-pyridine N-oxide, such as 4-acetyl-pyridine N-oxide, then converting the resulting acetyl-pyridine N-oxide, such as 4-acetyl-pyridine N-oxide, with dimethylformamide diethylacetal, which, for example, simultaneously serves as solvent, for example at approximately 110° C., into 3-dimethylamino-1-(N-oxido-pyridyl)-2-propen-1-one, such as 3-dimethylamino-1-(N-oxido-4-pyridyl)-2-propen-1-one, and then reacting the latter with an $R_2$-phenyl-guanidine wherein $R_2$ is as defined above, or preferably with a suitable salt, for example a nitrate, thereof in a suitable solvent, such as isopropanol, and in the presence of a suitable base, such as sodium hydroxide, for example under reflux, to form a compound of formula VIII.

In another method of preparing the starting material of formula VIII, the above-mentioned acetyl-pyridine N-oxide, such as 4-acetyl-pyridine N-oxide, is converted with phosphorus oxychloride in a suitable inert solvent, such as toluene, for example at approximately 100° C., first into acetyl-2-chloro-pyridine, for example 4-acetyl-2-chloro-pyridine. The resulting acetyl-2-chloro-pyridine, for example 4-acetyl-2-chloro-pyridine, is then converted with dimethylformamide diethylacetal, which, for example, simultaneously serves as solvent, for example at approximately 110° C., into 3-dimethylamino-1-(2-chloro-pyridyl)-2-propen-1-one, such as 3-dimethylamino-1-(2-chloro-4-pyridyl)-2-propen-1-one, which is then reacted with a suitable salt, for example a nitrate, of an $R_2$-phenyl-guanidine, wherein $R_2$ is as defined above, in a suitable solvent, such as isopropanol, and in the presence of a suitable base, such as sodium hydroxide, for example under reflux, to form a compound of formula VIII.

Process e

A reagent that introduces chlorine in the ortho-position with respect to the N-oxido group is, for example, phosphorus pentachloride, trifluoromethylsulfonyl chloride/HCl gas or preferably phosphorus oxychloride. By reacting a compound of formula VIII (for preparation see above under Process d) with such a reagent, such as especially phosphorus oxychloride, a compound of formula I is obtained wherein $R_1$ is a chlorine-substituted pyridyl radical that no longer contains an N-oxido group. The reaction with phosphorus oxychloride can be carried out, for example, in the absence of a solvent at approximately 100° C. Alternatively, it is possible to use phosphorus oxychloride together with a suitable amine, such as diisopropylamine, in a suitable solvent, for example a chlorinated hydrocarbon, such as chloroform, at approximately room temperature. Another possibility is to use phosphorus oxychloride in a suitable solvent, such as chloroform, toluene or xylene, at elevated temperature, for example under reflux.

Acid addition salts of compounds of formula I are obtained in customary manner, for example by treatment with an acid or a suitable anion exchange reagent.

Acid addition salts can be converted in customary manner into the free compounds, for example by treatment with a suitable basic agent.

Mixtures of isomers can be separated into the individual isomers in a manner known per se, for example by fractional crystallisation, chromatography, etc.

The processes described above, including the processes for removing protecting groups and the additional process measures are, unless otherwise indicated, carried out in a manner known per se for example in the presence or absence of preferably inert solvents or diluents, if necessary in the presence of condensation agents or catalysts, at reduced or elevated temperature, for example in a temperature range of from approximately −20° C. to approximately 150° C., especially from approximately 0° C. to approximately +70° C., preferably from approximately +10° C. to approximately +50° C., principally at room temperature, in a suitable vessel and, if necessary, in an inert gas atmosphere, for example a nitrogen atmosphere.

Taking into account all the substituents in the molecule, if necessary, for example if readily hydrolysable radicals are present, especially mild reaction conditions are to be used, such as short reaction times, the use of mild acidic or basic agents in low concentration, stoichiometric ratios, and the selection of suitable catalysts, solvents, temperature conditions and/or pressure conditions.

The invention relates also to those forms of the process in which a compound obtainable as intermediate at any stage of the process is used as starting material and the remaining process steps are carried out or the process is discontinued at any stage or a starting material is formed under the reaction conditions or is used in the form of a reactive derivative or salt. The starting materials used are preferably those which, according to the process, result in the compounds described above as being especially valuable.

The present invention relates also to novel starting materials and/or intermediates and to processes for the preparation thereof. The starting materials used and the reaction conditions chosen are preferably such that the compounds described in this Application as being especially preferred are obtained.

The invention relates also to a method of treating warm-blooded animals suffering from a tumour disease, which method comprises administering to warm-blooded animals requiring such treatment an amount that is effective in inhibiting tumours of a compound of formula I or of a pharmaceutically acceptable salt thereof. The invention relates also to the use of a compound of formula I or of a pharmaceutically acceptable salt thereof in the inhibition of protein kinase C in warm-blooded animals or in the preparation of pharmaceutical compositions for use in the therapeutic treatment of the human or animal body. Depending on the species, age, individual condition, mode of administration and the particular clinical picture, effective doses, for example daily doses of approximately 1–1000 mg, especially 50–500 mg, are administered to a warm-blooded animal of approximately 70 kg body weight.

The invention relates also to pharmaceutical compositions comprising an effective amount, especially an mount effective in the prophylaxis or treatment of one of the above-mentioned disorders, of the active ingredient together with pharmaceutically acceptable carriers that are suitable for topical, enteral, for example oral or rectal, or parenteral administration and that may be inorganic or organic, solid or liquid. There are used for oral administration especially tablets or gelatin capsules that comprise the active ingredient together with diluents, for example lactose, dextrose, sucrose, mannitol, sorbitol, cellulose and/or glycerol, and/or lubricants, for example silica, talc, stearic acid or salts thereof, such as magnesium or calcium stearate, and/or polyethylene glycol.

Tablets may also comprise binders, for example magnesium aluminium silicate, starches, such as corn, wheat or rice starch, gelatin, methylcellulose, sodium carboxymethylcellulose and/or polyvinylpyrrolidone, and, if desired, disintegrators, for example starches, agar, alginic acid or a salt thereof, such as sodium alginate, and/or effervescent mixtures, or adsorbents, dyes, flavourings and sweeteners. It is also possible to use the pharmacologically active compounds of the present invention in the form of parenterally administrable compositions or in the form of infusion solutions. Such solutions are preferably isotonic aqueous solutions or suspensions which, for example in the case of lyophilised compositions that comprise the active ingredient alone or together with a carrier, for example mannitol, can be made up prior to use. The pharmaceutical compositions may be sterilized and/or may comprise excipients, for example preservatives, stabilisers, wetting agents and/or emulsifiers, solubilisers, salts for regulating the osmotic pressure and/or buffers. The present pharmaceutical compositions, which may, if desired, comprise other pharmacologically active substances, such as antibiotics, are prepared in a manner known per se, for example by means of conventional mixing, granulating, confectioning, dissolving or lyophilising processes, and comprise approximately from 1% to 100%, especially from approximately 1% to approximately 20%, active ingredient(s).

The following Examples illustrate the invention without limiting it in any way. The $R_f$ values are determined on silica gel thin-layer plates (Merck, Darmstadt, Germany). The ratio of the eluants in the eluant mixtures used is indicated in parts by volume (v/v) and temperatures are indicated in degrees Celsius.

Abbreviations

HV: high vacuum

RT: room temperature

EXAMPLE 1

31 mg (0.78 mmol) of sodium hydroxide are added to a suspension of 150 mg (0.7 mmol) of 3-dimethylamino-1-(2-chloro-4-pyridyl)-2-propen-1-one and 165 mg (0.71 mmol) of 3-chloro-phenyl-guanidine nitrate in 1.5 ml of 2-propanol. After stirring under reflux for 18 hours, the reaction mixture is cooled and filtered and the material retained on the filter is washed thoroughly with water. After drying (60°, HV), N-(3-chloro-phenyl)-4-(2-chloro-4-pyridyl)-2-pyrimidineamine is obtained; m.p. 196°–198°, $R_f$=0.67 (methylene chloride:methanol=95:5), FAB-MS: 317 ($M^+$+1).

The starting material is obtained in the following manner:

Stage 1.1

4.12 ml (39.12 mmol) of 3-chloro-aniline are placed in 25 ml of ethanol, and 3.3 g (78.4 mmol) of cyanamide are added. 5.3 ml (62.7 mmol) of concentrated hydrochloric acid are added dropwise to the brown solution. The reaction solution is then stirred for 20 hours at 78°. After concentration under reduced pressure, the residue is dissolved in 25 ml of water, and 6.3 g (78.4 mmol) of ammonium nitrate are added. The precipitated substance is isolated by filtration, washed with water and dried at 60° under HV. 3-chloro-phenyl-guanidine nitrate is obtained; $^1$H-NMR (dimethyl sulfoxide): 7.2–7.8 (7H,m), 9.9 (1H,br,s).

Stage 1.2

24.61 g (177.62 mmol) of 2-chloro-4-cyano-pyridine are placed in 1.25 liters of diethyl ether under nitrogen, and 120 ml (22% in tetrahydrofuran, 353 mmol) of methylmagnesium chloride are added. The red suspension is stirred for 40 hours at RT, poured onto 1.25 liters of ice/water and 250 ml of 6N hydrochloric acid and stirred for 14 hours at RT. Extraction with diethyl ether and methylene chloride, drying with MgSO$_4$ and concentration give 4-acetyl-2-chloro-pyridine; R$_f$=0.5 (methylene chloride:methanol=9:1).

Stage 1.3

16.2 g (104.2 mmol) of 4-acetyl-2-chloro-pyridine are stirred for 1 hour at 110° with 116 ml of dimethylformamide diethylacetal. After cooling to 0°, filtering and drying at 60° under HV, 3-dimethylamino-1-(2-chloro-4-pyridyl)-2-propen-1-one is obtained; $^1$H-NMR (dimethyl sulfoxide): 2.98 (3H,s), 3.2 (3H,s), 5.9 (1H,d), 7.8 (3H,m), 8.5 (1H,d).

EXAMPLE 2

Analogously to Example 1 there is obtained from 150 mg (0.7 mmol) of 3-dimethylamino-1-(3-chloro4-pyridyl)-2-propen-1-one and 190 mg (0.71 mmol) of 3-trifluoromethyl-phenyl-guanidine nitrate N-(3-trifluoromethyl-phenyl)-4-(2-chloro-4-pyridyl)-2-pyrimidineamine; m.p. 168°–171°, R$_f$0.67 (methylene chloride:methanol=95:5).

The starting material is obtained in the following manner:

Stage 2.1

Analogously to Stage 1.1 there is obtained from 16.1 g (0.1 mol) of 3-trifluoromethyl-aniline and 6.3 g (0.15 mol) of cyanamide 3-trifluoromethyl-phenyl-guanidine nitrate; $^1$H-NMR (DMSO): 7.6 (7H,m), 9.9 (1H,br,s).

EXAMPLE 3

0.8 g (2.41 mmol) of N-(3-trifluoromethyl-phenyl)-4-(N-oxido4-pyridyl)- 2-pyrimidineamine is suspended in 40 ml of acetonitrile. 0.834 ml (6.65 mmol) of tri-methylsilyl cyanide and 0.611 ml (6.665 mmol) of dimethylcarbamoyl chloride are added and the reaction mixture is stirred for 12 hours at 60°. After concentration under reduced pressure, crystallisation is effected from tetrahydrofuran/diethyl ether. N-(3-trifluoromethyl-phenyl)-4-(2-cyano-4-pyridyl)-2-pyrimidineamine is obtained; m.p. 164°–166°, R$_f$=0.40 (n-hexane:ethyl acetate=1:1).

The starting material is obtained in the following manner:

Stage 3.1

15.1 g (0.0567 mmol) of 3-trifluoromethyl-phenyl-guanidine nitrate and 2.84 g (70.9 mmol) of sodium hydroxide are added to a suspension of 10 g (56.7 mmol) of 3-dimethylamino-1-(4-pyridyl)-2-propen-1-one [described in EP-A-0 233 461] in 300 ml of isopropanol The reaction mixture is boiled under reflux for 24 hours. After cooling, the product is isolated by filtration, washed with water and dried at 60° under HV. N-(3-trifluoromethyl-phenyl)-4-pyridyl-2-pyrimidineamine is obtained; m.p. 197°–198°, R$_f$=0.58 (ethyl acetate).

Stage 3.2

10.57 g (33.4 mmol) of N-(3-trifluoromethyl-phenyl)-4-pyridyl-2-pyrimidineamine are suspended in 200 ml of methylene chloride, and 10.49 g (33.42 mmol, 55% strength) of m-chloroperbenzoic acid are added. After 2 hours, 200 ml of water are added. The reaction product is isolated by filtration, washed with sodium carbonate solution and water and, after drying, N-(3-trifluoromethyl-phenyl)-4-(N-oxido-4-pyridyl)-2-pyrimidineamine is obtained. More product is obtained by chromatography (methylene chloride:methanol=9: 1) of the concentrated mother liquor; R$_f$=0.16 (methylene chloride:methanol=9:1).

EXAMPLE 4

100 mg (0.293 mmol) of N-(3-trifluoromethyl-phenyl)-4-(2-cyano4-pyridyl)-2-pyrimidineamine are stirred in 15 ml of ethanol and 15 ml of 2N sodium hydroxide solution for 3 hours at 60°. After acidifying with 4N hydrochloric acid, N-(3-trifluoromethyl-phenyl)-4-(2-carboxy-4-pyridyl)-2-pyrimidineamine is obtained; m.p. 241°–245°, FAB-MS: 361 (M$^+$+H).

EXAMPLE 5

500 mg (1.67 mmol) of N-(3-chloro-phenyl)-4-(N-oxido-4-pyridyl)-2-pyrimidineamine are suspended in 5 ml of acetonitrile, and 0.42 ml (4.5 mmol) of dimethylcarbamoyl chloride and 0.56 ml (4.5 mmol) of trimethylsilyl cyanide are added. After stirring for 14 hours at 60°, the reaction mixture is cooled to RT and the reaction product is isolated by filtration and washed with diethyl ether. Recrystallisation from tetrahydrofuran gives N-(3-chloro-phenyl)-4-(2-cyano-4-pyridyl)-2-pyrimidineamine in the form of yellow crystals; m.p. 221°–222°, R$_f$=0.6 (hexane:ethyl acetate=1:1).

The starting material is obtained in the following manner:

Stage 5.1

2.8 g (12 mmol) of 3-chloro-phenyl-guanidine nitrate and 0.5 g (12 mmol) of sodium hydroxide are added to a suspension of 2.0 g (11.7 mmol) of 3-dimethylamino-1-(4-pyridyl)-2-propen-1-one [described in EP-A-0 233 461] in 100 ml of isobutanol and the reaction mixture is boiled under reflux for 5 hours. After cooling, the reaction product is isolated by filtration, washed with water and chromatographed (tetrahydrofuran). After crystallisation (tetrahydrofuran/diethyl ether), N-(3-chloro-phenyl)-4-pyridyl-2-pyrimidineamine is obtained; m.p. 167°–168°, R$_f$=0.38 (methylene chloride:methanol=9:1).

Stage 5.2

1.0 g (3.54 mmol) of N-(3-chloro-phenyl)-4-(pyridyl)-2-pyrimidineamine are suspended in 50 ml of methylene chloride, and 1.1 g of m-chloroperbenzoic acid (50% strength) are added. After stirring for 18 hours at RT, the reaction mixture is filtered, the residue is dissolved in ethyl acetate/tetrahydrofuran (1:1) and extracted with 1N sodium hydroxide solution and water. The dried organic phase is concentrated and the residue is crystallised from diethyl ether/tetrahydrofuran to give N-(3-chloro-phenyl)-4-(N-oxido-4-pyridyl)-2-pyrimidineamine; m.p. 268°–270°, R$_f$=0.6 (methylene chloride:methanol=9:1).

EXAMPLE 6

50 mg (0.16 mmol) of N-(3-chloro-phenyl)-4-(2-cyano-4-pyridyl)-2-pyrimidineamine are stirred in 5 ml of ethanol and 5 ml of 2N sodium hydroxide solution for 2 hours at 60°. After cooling to RT, the product is isolated by filtration and washed with ethanol/water (9:1) and dried at 50° under HV. The sodium salt of N-(3-chloro-phenyl)-4-(2-carboxy-4-pyridyl)-2-pyrimidineamine is obtained; m.p. >250°, $R_f$=<0.1 (methylene chloride:methanol=9:1).

EXAMPLE 7

50 mg (0.16 mmol) of N-(3-chloro-phenyl)-4-(2-cyano-4-pyridyl)-2-pyrimidineamine are suspended in 2 ml of methanol. 0.58 ml of hydrogen peroxide (30% strength), 0.16 ml of 1-hexene and 11 mg of sodium carbonate are added and the reaction mixture is stirred for 14 hours at RT. The product is isolated by filtration, washed (methanol:water=1:1) and dried at 50° under HV. N-(3-chloro-phenyl)-4-(2-carbamoyl-4-pyridyl)-2-pyrimidineamine is obtained in the form of a yellow powder; m.p. 245°–247°, $R_f$=0.23 (n-hexane:ethyl acetate=1:1).

EXAMPLE 8

100 mg (0.293 mmol) of N-(3-trifluoromethyl-phenyl)-4-(2-cyano-4-pyridyl)-2-pyrimidineamine are suspended in 4 ml of methanol. 1.1 ml of hydrogen peroxide (30%), 0.32 ml of 1-hexene and 22 mg of sodium carbonate are added and the reaction mixture is stirred for 16 hours at RT. The product is isolated by filtration and washed (methanol/water) to give N-(3-trifluoromethyl-phenyl)-4-(2-carbamoyl-4-pyridyl)-2-pyrimidineamine; m.p. 240°–242°, FAB-MS: 360 ($M^+$+H).

EXAMPLE 9

In a manner analogous to that described above and by simple conversion reactions, known per se, of the products, the following compounds are prepared:
a) N-(3-chloro-phenyl)-4-(2-n-propylamino-4-pyridyl)-2-pyrimidineamine,
b) N-(3-chloro-phenyl)-4-(2-amino-4-pyridyl)-2-pyrimidineamine,
c) N-(3-chloro-phenyl)-4-(2-hydroxy-4-pyridyl)-2-pyrimidineamine and
d) N-(3-chloro-phenyl)-4-(2-methoxy-4-pyridyl)-2-pyrimidineamine.

EXAMPLE 10

300 mg (0.95 mmol) of N-(3-chloro-phenyl)-4-(2-chloro-4-pyridyl)-2-pyrimidineamine (see Example 1), 5.3 ml of 1,3-propanediol and 3.0 ml of dimethylformamide are stirred for 43 hours at 105°. After concentration and repeated chromatography (methylene chloride:methanol=98:2) N-(3-chloro-phenyl)-4-(2-dimethylamino-4-pyridyl)-2-pyrimidineamine is obtained; m.p. 176°–178°, FAB-MS: 326 ($M^+$+H).

EXAMPLE 11

14.5 g (53.7 mmol) of 3-ethoxycarbonyl-phenyl-guanidine nitrate, 11.3 g (53.7 mmol) of 3-dimethylamino-1-(2-chloro-4-pyridyl)-2-propen-1-one and 2.4 g (60 mmol) of sodium hydroxide are stirred in 150 ml of isobutanol for 14 hours at 110°. After cooling, washing twice with 100 ml of ethanol each time and crystallising (tetra-hydrofuran/ethanol), N-[3-ethoxycarbonyl-phenyl]-4-(2-chloro-4-pyridyl)-2-pyrimidineamine is obtained; m.p. 149°–150°, FAB-MS: 355 ($M^+$+H).

EXAMPLE 12

N-[3-isopropoxycarbonyl-phenyl]-4-(2-chloro-4-pyridyl)-2-pyrimidineamine is isolated as a secondary product of Example 11; m.p. 130°–131°, FAB-MS: 383 ($M^+$+H).

EXAMPLE 13

9.4 g (26.5 mmol) of N-[3-ethoxycarbonyl-phenyl]-4-(2-chloro-4-pyridyl)-2-pyrimidineamine (see Example 11) and 50 ml of 2N sodium hydroxide solution are boiled under reflux in 300 ml of ethanol for 1 hour. After cooling to RT, the reaction mixture is acidified (4N hydrochloric acid) and the reaction product is isolated by filtration. After drying at 50° under HV, lemon-yellow crystals of N-[3-carboxy-phenyl]-4-(2-chloro-4-pyridyl)-2-pyrimidineamine are obtained; m.p. 267°–268°, FAB-MS: 327 ($M^+$+H).

EXAMPLE 14

Analogously to Example 1 there is obtained from 100 mg (0.32 mmol) of N-[3-chloro-phenyl]-4-(2-chloro-4-pyridyl)-2-pyrimidineamine and 3 ml (29.9 mmol) of n-1-butylamine N-[3-chloro-phenyl]-4-[2-(n-1-butylamino)-4-pyridyl]-2-pyrimidineamine; m.p. 151°–158°, FAB-MS: 354 ($M^+$+H).

EXAMPLE 15

Tablets each comprising 20 mg of active ingredient, for example one of the compounds of formula I described in Examples 1–14, are prepared with the following composition in customary manner:

| Composition: | |
| --- | --- |
| active ingredient | 20 mg |
| wheat starch | 60 mg |
| lactose | 50 mg |
| colloidal silica | 5 mg |
| talc | 9 mg |
| magnesium stearate | 1 mg |
| | 145 mg |

Preparation

The active ingredient is mixed with a portion of the wheat starch, with the lactose and with the colloidal silica, and the mixture is forced through a sieve. A further portion of the wheat starch is made into a paste with 5 times the amount of water on a water bath, and the powder mixture is kneaded with the paste until a slightly plastic mass has been formed.

The plastic mass is pressed through a sieve of approximately 3 mm mesh size and dried, and the resulting dry granules are forced through a sieve again. The remainder of the wheat starch, the talc and the magnesium stearate are admixed and the mixture is compressed to form tablets each weighing 145 mg and having a breaking notch.

EXAMPLE 16

Capsules each comprising 10 mg of active ingredient, for example one of the compounds of formula I described in Examples 1–14, are prepared in customary manner as follows:

| Composition: | |
| --- | --- |
| active ingredient | 2500 mg |
| talc | 200 mg |
| colloidal silica | 50 mg |

Preparation

The active ingredient is intimately mixed with the talc and the colloidal silica, and the mixture is forced through a sieve 0.5 mm mesh size and introduced in 11-mg portions into hard gelatin capsules of suitable size.

What is claimed is:

1. An N-phenyl-2-pyrimidineamine derivative of formula I

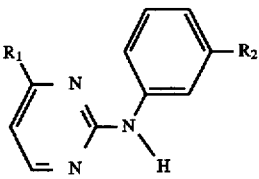 (I)

wherein

R₁ is a substituted cyclic radical, the cyclic radical being bonded at a ring carbon atom in each case and being selected from pyridyl, pyrazinyl, thiazolyl, pyrimidinyl, pyridazinyl and imidazolyl, and the substituents of the above-mentioned cyclic radical being selected from one or more of the groups halogen, cyano, carbamoyl, —C(=O)—OR₃, —C(=O)—R₄, —SO₂—N(R₅)—R₆, —N(R₇)—R₈, —OR₉ and fluorine-substituted lower alkyl, wherein R₃, R₄, R₅, R₆, R₇, R₈ and R₉ are each independently of the others hydrogen or lower alkyl that is unsubstituted or substituted by mono- or di-lower alkylamino; and R₂ is selected from halogen, cyano, carbamoyl, —C(=O)—OR₁₀, —C(=O)—R₁₁, —SO₂—N(R₁₂)—R₁₃, —N(R₁₄)—R₁₅, —OR₁₆ and fluorine-substituted lower alkyl, wherein R₁₀, R₁₁, R₁₂, R₁₃, R₁₄, R₁₅ and R₁₆ are each independently of the others hydrogen or lower alkyl that is unsubstituted or substituted by mono- or di-lower alkylamino, or a salt of such a compound having at least one salt-forming group.

2. A compound according to claim 1 of formula I, wherein

R₁ is substituted pyridyl bonded to a ring carbon atom, the substituents of the above-mentioned pyridyl radical being selected from halogen, cyano, carbamoyl, —C(=O)—OR₃, —N(R₇)—R₈ and —OR₉, wherein R₃, R₇, R₈ and R₉ are each independently of the others hydrogen or lower alkyl; and R₂ is selected from halogen, —C(=O)—OR₁₀, wherein R₁₀ is hydrogen or lower alkyl, and from fluorine-substituted lower alkyl, or a salt of such a compound having at least one salt-forming group.

3. A compound according to claim 1 of formula I, wherein

R₁ is a pyridyl radical substituted by halogen, cyano, carboxy, carbamoyl, hydroxy or by N-lower alkylamino, and R₂ is halogen or fluorine-substituted lower alkyl, or a salt thereof.

4. A compound according to claim 1 of formula I, wherein

R₁ is a 4-pyridyl radical substituted in the 2-position with respect to the pyridine nitrogen by chlorine, cyano, carboxy, carbamoyl, hydroxy or by N-propyl-amino and R₂ is chlorine or trifluoromethyl, or a salt thereof.

5. A compound according to claim 1 of formula I, wherein

R₁ is a 4-pyridyl radical substituted in the 2-position with respect to the pyridine nitrogen by chlorine, cyano, carboxy, carbamoyl, hydroxy, amino, N-propyl-amino, N,N-dimethylamino or by N-butyl-amino, and R₂ is chlorine, trifluoromethyl, carboxy or lower alkoxycarbonyl, or a salt thereof.

6. A compound according to claim 1 of formula I or a pharmaceutically acceptable salt of such a compound having at least one salt-forming group, selected from N-(3-chloro-phenyl)-4-(2-chloro4-pyridyl)-2-pyrimidineamine, N-(3-trifluoromethyl-phenyl)-4-(2-chloro-4-pyridyl)-2-pyrimidineamine, N-(3-trifluoromethyl-phenyl)-4-(2-cyano-4-pyridyl)-2-pyrimidineamine, N-(3-trifluoromethyl-phenyl)-4-(2-carboxy-4-pyridyl)-2-pyrimidineamine, N-(3-chloro-phenyl)-4-(2-cyano-4-pyridyl)-2-pyrimidineamine, N-(3-chloro-phenyl)-4-(2-carboxy-4-pyridyl)-2-pyrimidineamine, N-(3-chloro-phenyl)-4-(2-carbamoyl-4-pyridyl)-2-pyrimidineamine, N-(3-trifluoromethyl-phenyl)-4-(2-carbamoyl-4-pyridyl)-2-pyrimidineamine, N-(3-chloro-phenyl)-4-(2-n-propylamino-4-pyridyl)-2-pyrimidineamine, N-(3-chloro-phenyl)-4-(2-amino-4-pyridyl)-2-pyrimidineamine, N-(3-chloro-phenyl)-4-(2-hydroxy-4-pyridyl)-2-pyrimidineamine, N-(3-chloro-phenyl)-4-(2-dimethylamino-4-pyridyl)-2-pyrimidineamine, N-[3-ethoxycarbonyl-phenyl]-4-(2-chloro-4-pyridyl)-2-pyrimidineamine, N-[3-isopropoxycarbonyl-phenyl]-4-(2-chloro-4-pyridyl)-2-pyrimidineamine, N-[3-carboxy-phenyl]-4-(2-chloro-4-pyridyl)-2-pyrimidineamine and N-[3-chloro-phenyl]-4-[2-(n-1-butylamino)-4-pyridyl]-2-pyrimidineamine, and from the pharmaceutically acceptable salts of such compounds having at least one salt-forming group.

7. A compound of formula I according to claim 1, or a pharmaceutically acceptable salt thereof, said compound being N-(3-chloro-phenyl)-4-(2-amino-4-pyridyl)-2-pyrimidineamine.

8. A pharmaceutical composition comprising a compound of formula I according to claim 1 or a pharmaceutically acceptable salt of such a compound having at least one salt-forming group together with a pharmaceutical carrier.

9. A process for the preparation of an N-phenyl-2-pyrimidineamine derivative of formula I

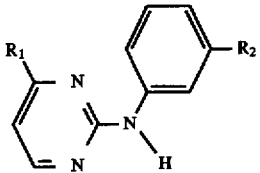 (I)

wherein

R₁ is a substituted cyclic radical, the cyclic radical being bonded at a ring carbon atom in each case and being selected from pyridyl, pyrazinyl, thiazolyl, pyrimidinyl, pyridazinyl and imidazolyl, and the substituents of the above-mentioned cyclic radical being selected from one or more of the groups halogen, cyano, carbamoyl, —C(=O)—OR$_3$, —C(=O)—R$_4$, —SO$_2$—N(R$_5$)—R$_6$, —N(R$_7$)—R$_8$, —OR$_9$ and fluorine-substituted lower alkyl, wherein R$_3$, R$_4$, R$_5$, R$_6$, R$_7$, R$_8$ and R$_9$ are each independently of the others hydrogen or lower alkyl that is unsubstituted or substituted by mono- or di-lower alkylamino; and R$_2$ is selected from halogen, cyano, carbamoyl, —C(=O)—OR$_{10}$, —C(=O)—R$_{11}$, —SO$_2$—N(R$_{12}$)—R$_{13}$, —N(R$_{14}$)—R$_{15}$, —OR$_{16}$ and fluorine-substituted lower alkyl, wherein R$_{10}$, R$_{11}$, R$_{12}$, R$_{13}$, R$_{14}$, R$_{15}$ and R$_{16}$ are each independently of the others hydrogen or lower alkyl that is unsubstituted or substituted by mono- or di-lower alkylamino, or of a salt of such a compound having at least one salt-forming group, wherein a compound of formula II

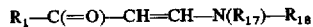

R$_1$—C(=O)—CH=CH—N(R$_{17}$)—R$_{18}$ (II), wherein R$_{17}$ and R$_{18}$ are each independently of the other lower alkyl and R$_1$ is as defined above, functional groups present in a compound of formula II, with the exception of the groups participating in the reaction, being, if necessary, in protected form, or a salt of such a compound is reacted with a compound of formula III

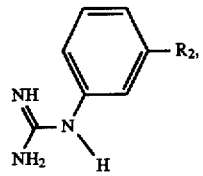

(III)

wherein R$_2$ is as defined above, functional groups present in a compound of formula III, with the exception of the guanidino group participating in the reaction, being, if necessary, in protected form, or with a salt of such a compound, and any protecting groups present are removed and, if desired, a compound of formula I obtainable in accordance with the above process is converted into its salt, or an obtainable salt of a compound of formula I is converted into the free compound.

* * * * *